(12) United States Patent
Seguin et al.

(10) Patent No.: US 8,632,585 B2
(45) Date of Patent: Jan. 21, 2014

(54) APPARATUS FOR TREATING A HEART VALVE, IN PARTICULAR A MITRAL VALVE

(75) Inventors: Jacques Seguin, Windsor (GB); Bruno Lecointe, Rueil Malmaison (FR); Remi Gerriet, Paris (FR)

(73) Assignee: Medtronic CoreValve, Inc., Minneapolis, MN (US)

( * ) Notice: Subject to any disclaimer, the term of this patent is extended or adjusted under 35 U.S.C. 154(b) by 0 days.

(21) Appl. No.: 13/572,226

(22) Filed: Aug. 10, 2012

(65) Prior Publication Data

US 2013/0035758 A1 Feb. 7, 2013

Related U.S. Application Data

(62) Division of application No. 12/481,350, filed on Jun. 9, 2009, now Pat. No. 8,262,724.

(60) Provisional application No. 61/129,170, filed on Jun. 9, 2008.

(30) Foreign Application Priority Data

Apr. 18, 2008 (FR) ...................................... 08 02164

(51) Int. Cl.
*A61F 2/24* (2006.01)
(52) U.S. Cl.
USPC ...................................................... 623/2.11
(58) Field of Classification Search
USPC ............ 600/37; 606/139, 144–148, 157, 158, 606/232, 214–217, 108, 151, 213, 219, 300, 606/329; 623/2.36, 1.11, 1.12, 1.23, 1.3, 623/2.11, 2.38, 2.4, 2.1
See application file for complete search history.

(56) References Cited

U.S. PATENT DOCUMENTS

| 5,242,457 | A | 9/1993 | Akopov et al. |
| 6,210,432 | B1 | 4/2001 | Solem et al. |
| 6,332,893 | B1 | 12/2001 | Mortier et al. |
| 6,602,288 | B1 | 8/2003 | Cosgrove et al. |
| 6,689,164 | B1 | 2/2004 | Seguin |
| 6,702,835 | B2 | 3/2004 | Ginn |
| 6,723,038 | B1 | 4/2004 | Schroeder et al. |
| 6,776,784 | B2 | 8/2004 | Ginn |

(Continued)

FOREIGN PATENT DOCUMENTS

| WO | WO2008/038276 | 4/2008 |
| WO | WO2008/129405 | 10/2008 |

OTHER PUBLICATIONS

"Keyhole Surgery definition" www.thefreedictionary.com accessed on Jul. 9, 2013.*

*Primary Examiner* — Ryan Severson
*Assistant Examiner* — Rachel S Papeika (57) ABSTRACT

An apparatus for treating a heart valve apparatus includes at least two anchoring elements designed to be anchored at the annulus and/or heart wall of the valve to be treated. Each anchoring element has a support surface. At least one linking element includes a central branch and two curved side branches, one of which is designed to be engaged on the support surface of an anchoring element, while the other is designed to be engaged on the support surface of another anchoring element, the linking element then being designed to be pivoted to a position such that the anchoring elements interconnect and in which the ends of the central branch are located in the vicinity of the support surfaces.

13 Claims, 7 Drawing Sheets

(56) References Cited

U.S. PATENT DOCUMENTS

| | | |
|---|---|---|
| 6,962,605 B2 | 11/2005 | Cosgrove et al. |
| 6,986,775 B2 | 1/2006 | Morales et al. |
| 6,986,784 B1 | 1/2006 | Weiser et al. |
| 6,989,028 B2 | 1/2006 | Lashinski et al. |
| 6,997,950 B2 | 2/2006 | Chawla |
| 6,997,951 B2 | 2/2006 | Solem et al. |
| 7,011,682 B2 | 3/2006 | Lashinski et al. |
| 7,037,334 B1 | 5/2006 | Hlavka et al. |
| 7,044,967 B1 | 5/2006 | Solem et al. |
| 7,056,325 B1 | 6/2006 | Makower et al. |
| 7,090,695 B2 | 8/2006 | Solem et al. |
| 7,166,127 B2 | 1/2007 | Spence et al. |
| 7,211,110 B2 | 5/2007 | Rowe et al |
| 7,220,265 B2 | 5/2007 | Chanduszko et al. |
| 7,296,577 B2 | 11/2007 | Lashinski et al. |
| 7,311,728 B2 | 12/2007 | Solem et al. |
| 7,431,692 B2 | 10/2008 | Zollinger et al. |
| 7,431,726 B2 | 10/2008 | Spence et al. |
| 7,588,582 B2 | 9/2009 | Starksen et al. |
| 7,635,386 B1 | 12/2009 | Gammie |
| 7,637,945 B2 | 12/2009 | Solem et al. |
| 7,666,193 B2 | 2/2010 | Starksen et al. |
| 7,699,892 B2 | 4/2010 | Rafiee et al. |
| 7,717,954 B2 | 5/2010 | Solem et al. |
| 7,758,637 B2 | 7/2010 | Starksen et al. |
| 2003/0105519 A1 | 6/2003 | Fasol et al. |
| 2004/0193191 A1 | 9/2004 | Starksen et al. |
| 2004/0220596 A1 | 11/2004 | Frazier et al. |
| 2004/0243227 A1 | 12/2004 | Starksen et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0177180 A1 | 8/2005 | Kaganov et al. |
| 2005/0187568 A1 | 8/2005 | Klenk et al. |
| 2005/0197696 A1 | 9/2005 | Duran |
| 2005/0267495 A1 | 12/2005 | Ginn et al. |
| 2005/0273138 A1 | 12/2005 | To et al. |
| 2006/0025787 A1 | 2/2006 | Morales et al. |
| 2006/0030885 A1 | 2/2006 | Hyde |
| 2006/0052821 A1 | 3/2006 | Abbott et al. |
| 2006/0095025 A1 | 5/2006 | Levine et al. |
| 2006/0276891 A1 | 12/2006 | Nieminen et al. |
| 2007/0010857 A1 | 1/2007 | Sugimoto et al. |
| 2007/0055206 A1 | 3/2007 | To et al. |
| 2007/0073315 A1 | 3/2007 | Ginn et al. |
| 2007/0112424 A1 | 5/2007 | Spence et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2008/0194939 A1* | 8/2008 | Dickinson et al. ............ 600/407 |
| 2008/0228032 A1 | 9/2008 | Starksen et al. |
| 2008/0228165 A1 | 9/2008 | Spence et al. |
| 2008/0228265 A1 | 9/2008 | Spence et al. |
| 2008/0228266 A1 | 9/2008 | McNamara et al. |
| 2008/0228267 A1 | 9/2008 | Spence et al. |
| 2008/0234701 A1 | 9/2008 | Morales et al. |
| 2008/0234702 A1 | 9/2008 | Morales et al. |
| 2008/0234704 A1 | 9/2008 | Starksen et al. |
| 2008/0234728 A1 | 9/2008 | Starksen et al. |
| 2008/0234815 A1 | 9/2008 | Starksen |
| 2008/0243150 A1 | 10/2008 | Starksen et al. |
| 2008/0275503 A1 | 11/2008 | Spence et al. |
| 2008/0294177 A1 | 11/2008 | To et al. |
| 2009/0076547 A1 | 3/2009 | Sugimoto et al. |
| 2009/0209950 A1 | 8/2009 | Starksen |
| 2009/0222083 A1 | 9/2009 | Nguyen et al. |
| 2009/0234318 A1 | 9/2009 | Loulmet et al. |
| 2009/0306755 A1* | 12/2009 | Dickinson et al. ............. 623/1.3 |
| 2010/0023056 A1 | 1/2010 | Johansson et al. |
| 2010/0030328 A1 | 2/2010 | Seguin et al. |
| 2010/0070028 A1 | 3/2010 | Sugimoto |
| 2010/0094248 A1 | 4/2010 | Nguyen et al. |
| 2010/0161042 A1 | 6/2010 | Maisano et al. |

* cited by examiner

APPARATUS FOR TREATING A HEART VALVE, IN PARTICULAR A MITRAL VALVE

This application is a Divisional of and claims the benefit of U.S. patent application Ser. No. 12/481,350, filed Jun. 9, 2009, now U.S. Pat. No. 8,262,724, which claims the benefit under 35 U.S.C. §119(e) of U.S. patent application Ser. No. 61/129,170, filed Jun. 9, 2008, both of which are incorporated herein by reference in their entirety. This application claims priority to FR 08 02164, filed Apr. 18, 2008.

The present invention relates to apparatus and methods for treating a heart valve, such as a mitral heart valve. The treatment in question may include performing an annuloplasty, i.e., reducing an annular distension or reinforcing the annulus of a normal or abnormal valve.

The annulus of a heart valve may, over time, undergo a distension that leads to poor coaptation of the valves, resulting in a loss of effective sealing of the valve.

To treat this condition, it is known that an annuloplasty can be done, i.e., the annulus can be recalibrated by means of an implant that is set in place over it.

The annuloplasty implant can be a prosthetic ring attached to the native valve annulus. However, existing implants of this type and their corresponding implantation techniques have the disadvantage of involving open-heart surgery.

The annuloplasty implant can also be a deformable elongate element that can be introduced by means of a catheter with a minimally invasive vascular approach, then delivered by the catheter and attached near the valve annulus before being retracted circumferentially. Existing annuloplasty implants of this type, and their corresponding implantation techniques, as well as the systems using the coronary sinuses, are not entirely satisfactory for recalibrating the annulus.

A percutaneous procedure that utilizes a catheter is another technique for implanting a prosthetic heart valve. Until now, percutaneously implanting an implant on the mitral valve of a heart has been difficult because the annulus of a mitral valve is elastic and may distend when a prosthetic valve is implanted percutaneously.

SUMMARY

Embodiments of the invention include anchoring elements designed to be anchored at the annulus of the valve to be treated and/or in the heart wall next to the annulus in such a way that they are spaced apart from each other, said anchoring elements each having a support surface, and at least one linking element comprising a central branch and two curved side branches, and systems and methods using such combinations of elements.

BRIEF DESCRIPTION OF THE DRAWINGS

The schematic drawings attached represent, in nonlimiting fashion, one embodiment of an apparatus and method of the invention.

DETAILED DESCRIPTION OF EMBODIMENTS

Preferably, one of the side branches extends at the level of one end of the central branch, on one side of the central branch, and the other side branch extends at the level of the other end of the central branch, on the opposite side of the central branch. One of said side branches may be engaged on the support surface of an anchoring element while the other side branch is engaged on the support surface of another anchoring element. Preferably, the linking element is pivotable in an axis perpendicular to the central branch to cause the side branches to slide along the respective support surfaces up to a position in which the anchoring elements interconnect and in which the ends of the central branch are located in the vicinity of said support surfaces.

Treatment of a heart valve may be accomplished by implanting at least two anchoring elements in the annulus of the valve to be treated and/or in the heart wall next to this annulus, then interconnecting the two anchoring elements by a linking element. The interconnection may be effected by bringing the side branches of the linking element into engagement with the support surfaces of the two anchoring elements and then causing this linking element to pivot in such a way as to bring the ends of the central branch near the respective support surfaces of the anchoring elements.

Such apparatus enables two distant anchoring elements to be connected to hold the two areas of tissue in which the anchoring elements are implanted with respect to each other, in a relatively simple and rapid manner. Embodiments of the invention are not limited to two anchoring elements and one linking element. For example, the embodiments may include two, three, four or more anchoring elements and more than one linking element, linked in a series with two ends or in a closed loop.

After implantation, a phenomenon known as "encapsulation," i.e., formation of a cicatricial fibrosis around the anchoring elements and/or the linking element, preferably occurs, ensuring that the linking element is held in position.

Preferably, the apparatus also includes a catheter for inserting and placing the linking element percutaneously, including structure for positioning the linking element that allows the side branches to come into engagement with the support surfaces of the anchoring elements, and structure for pivotably entraining the linking element.

The positioning and pivoting entrainment structure may, for example, include a mandrel engaged in a sheath which can pivot with respect to the sheath. The mandrel preferably has, at the level of its distal end, a diametrical groove that tightly receives the central branch of a linking element such that there is a reversible link between the mandrel and the linking element. The mandrel can be slid axially with respect to the sheath in order to extract the side branches out of the sheath. Then, after engagement of the side branches on the support surfaces, the mandrel is pivotable to effect the pivoting of the connecting element and hence the interconnection in the aforesaid manner. The mandrel can then be moved back relative to the sheath so as to be separated from the central branch.

Preferably, the apparatus also includes structure for enabling two anchoring elements to be implanted at a predetermined distance from each other.

This structure may include an implantation catheter, configured to place a first anchoring element and to place a second anchoring element, positioned with respect to each other. Such a catheter can, for example, place the first and second anchoring elements in two holes that have been previously created in the tissue. The two holes, each of which allows engagement of a mandrel for placement of an anchoring element, are spaced at a predetermined distance from each other.

In the case where two anchoring elements are placed at a predetermined distance from each other, the length of the central branch of the linking element may be equal to the predetermined distance. The linking element then provides maintenance of the two anchoring elements according to that predetermined distance so that the apparatus prevents the valve annulus from undergoing additional distension, or enables a mitral valve to be rendered non-elastic, for example, instead of placing a prosthetic heart valve.

The central branch can also have a smaller length than the predetermined distance, so that the linking element, when set in place, brings the two anchoring elements to which it is connected closer together. Such apparatus can effect a contraction of the heart annulus and hence an annuloplasty.

Preferably, at least one of the branches extends substantially in a plane oriented obliquely with respect to the lengthwise axis of the central branch.

In such embodiments, the free end of at least one side branch is thus located at a distance from the lengthwise axis, in a direction perpendicular to the lengthwise axis, such that it can be engaged on the corresponding support surface of an anchoring element while the central branch is at a distance from the anchoring element. This distance facilitates engagement of the lateral branches on the respective support surfaces of the anchoring elements. Moreover, the inclination of the branch can contribute to ensuring that the linking element is held in the interconnection position.

The side branches are preferably of identical lengths so that their ends are diametrically opposite each other.

Advantageously, at least one side branch may extend over an arc delimited by radii that form an angle of approximately 60 to 180° between them. The side branch is preferably of a substantial length, thereby ensuring that it is kept perfectly in engagement with the support surface on which it is engaged.

The length of at least one side branch may be such that the free end of the side branch is located in the extension of the lengthwise axis of the central branch.

Preferably, at least one side branch has an inclination and/or length such that, in the interconnection position, its free end engages in a corresponding cavity in the anchoring element. This engagement reinforces the holding of the side branch in the interconnection position relative to the anchoring element, thus generating a holding effect.

When at least one anchoring element is formed with a helically wound wire, as described below, the free end of the side branch preferably engages between two turns of the anchoring element.

The free end of at least one side branch is preferably sharp in order to facilitate its penetration into the cavity of the anchoring organ.

Advantageously, the linking element may have at least one receptacle between one end of the central branch and the corresponding end of a side branch, said receptacle being designed to receive and retain the support surface when the linking element is in the interconnection position. Hence, the linking element may be held in the interconnection position.

In embodiments, the linking element is made by shaping a single wire and the receptacle is created by shaping the wire in a hollow fashion between the respective ends of the central branch and the corresponding side branch.

In embodiments, at least one anchoring element has an extending part designed to extend out from the tissue after implantation of an anchoring element, the extending part being created by helical winding of a wire and having at least one turn through which one of the two side branches of the linking element can be engaged. The turn forms a support surface of the anchoring element.

Preferably, in this case, the turn has a diameter that is greater than the rest of the extending part. The increased diameter facilitates engagement of a side branch of the linking element in this turn.

At least one anchoring element preferably has an anchoring part designed to be anchored at the annulus of the valve to be treated and/or in the heart wall next to the annulus, said anchoring part being created by helical winding of a wire.

The anchoring element can thus be relatively easily and quickly implanted by screwing into the tissue, and the screwing can be effected percutaneously by way of an appropriate catheter.

Advantageously, in this case, the anchoring part is formed by several turns whose diameters decrease in the direction of the part of the anchoring element that includes the support surface.

Because of this reduction in the diameters of the turns in the screwing direction, placement of the anchoring element effects a contraction of the area of the tissue in which the anchoring element is implanted. The contraction ensures solid implantation of the anchoring element and contributes to reducing the annulus diameter.

Percutaneous procedures preferably include the following steps: implanting at least two anchoring elements at the annulus of the valve to be treated and/or in the heart wall next to the annulus, and interconnecting these two anchoring elements by way of the linking element.

Such methods may also include the step of implanting at least two anchoring elements at a predetermined distance from each other.

The methods may include the step of using at least one linking element whose central branch length is less than the predetermined distance.

Figure 1:
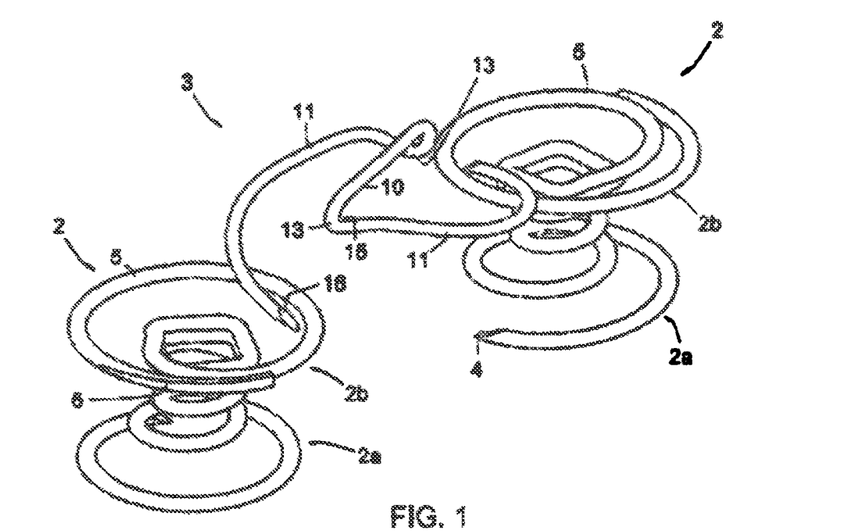
FIG. 1 is a perspective view of two anchoring elements and one linking element before implantation of the anchoring elements and before placement of the connecting element on the anchoring elements.
Figure 2:
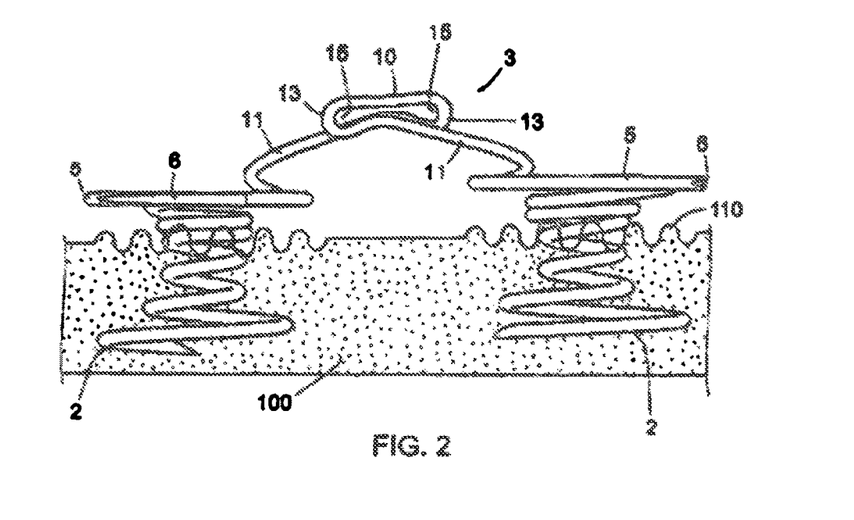
FIG. 2 is a side view after implantation of the anchoring elements and before placement of the connecting element on the anchoring elements.

FIGS. 1 and 2 depict two anchoring elements 2 and one linking element 3 which are part of an apparatus for treating a heart valve, in particular a mitral heart valve. The apparatus may also include an implantation catheter 20 (see FIGS. 7A-C and 8) enabling the two anchoring elements 2 to be implanted percutaneously at a predetermined distance from each other, and a catheter 30 (see FIGS. 9A, 9B and 10) for inserting and placing the linking element 3, also percutaneously. The apparatus may include more than two anchoring elements 2 and more than one linking element 3, optionally with the anchoring elements linked in a series of three, four, five, six or more, in a closed loop or open chain configuration, with each internal anchoring element in a series being respectively linked to two adjacent anchoring elements in the same manner as described below.

Each anchoring element 2 of the Figures is comprised of a wound metal wire, and has an anchoring part 2a designed to be inserted into the tissue 100 of the annulus of the valve to be treated and/or the heart wall next to this annulus, and an extending part 2b, designed to extend out from tissue 100 once the anchoring element 2 has been implanted.

The anchoring part 2a in these Figures is formed of three tarns whose diameters decrease in the direction of the extending part 2b, and the free end of the wire that terminates the part 2a has a bevel 4 making the end sharp.

The anchoring element 2 is designed to be implanted in the tissue 100 by screwing along its axis, this screwing preferably being effected percutaneously by use of the implantation catheter 20. Due to the reduction in diameter of the turns of part 2a in this screwing direction, placement of the anchoring element 2 causes a contraction 110 of the tissue area 100 in which the anchoring element 2 is implanted, as can be seen in FIG. 2.

The extending part 2b has, in the example shown, on the side of part 2a, two square turns and, on the side opposite this part 2a, a turn 5 with a greater diameter than that of the rest of said extending part 2b. The diameter can preferably be slightly greater than that of the largest turn of part 2a.

The wire that forms anchoring element 2 has, at its terminal part in turn 5, a bevel 6 extending over for example about one-fifth of the circumference of the turn 5, which sharply reduces the thickness of the wire at the free end of the wire. This free end can thus project radially only slightly with respect to turn 5.

The linking element 3 is also preferably formed by a single metal wire, shaped so as to constitute a central branch 10, two curved side branches 11, and two intermediate portions 13 that are intermediate between the central branch 10 and the side branches 11.

Figure 6:
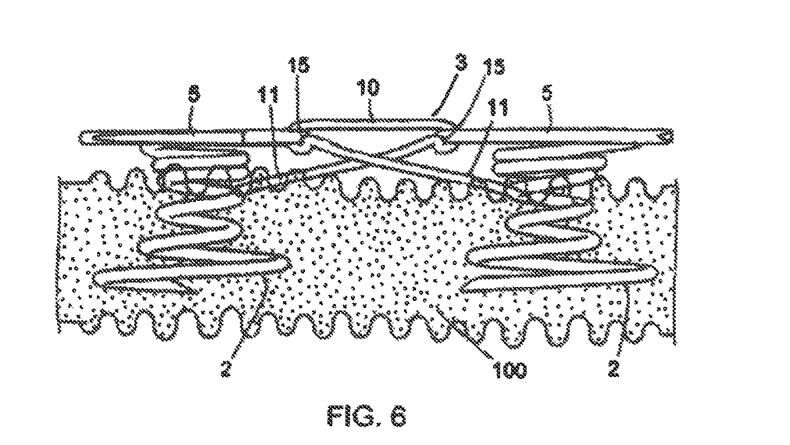
FIG. 6 is a view similar to that of FIG. 2 after the linking element has been placed on the anchoring elements.
Figure 7A:
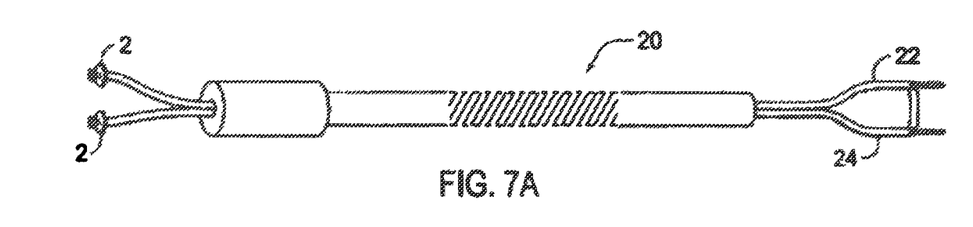
FIGS. 7A-C are views of the catheter for placing the anchoring elements.
Figure 7B:
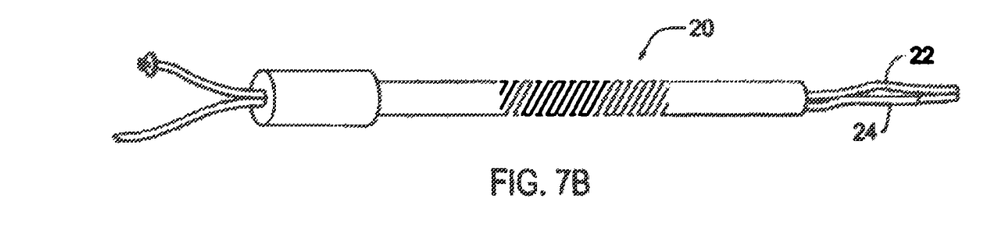
Figure 7C:
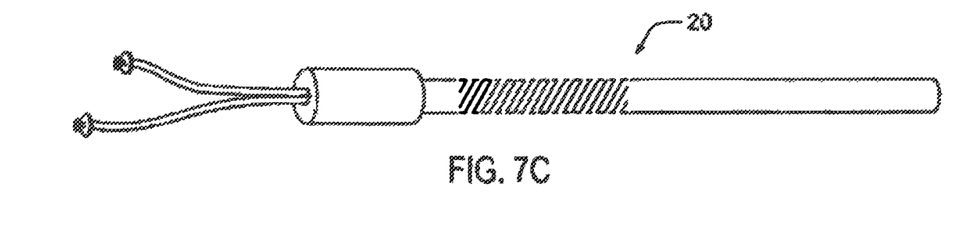
Figure 8:
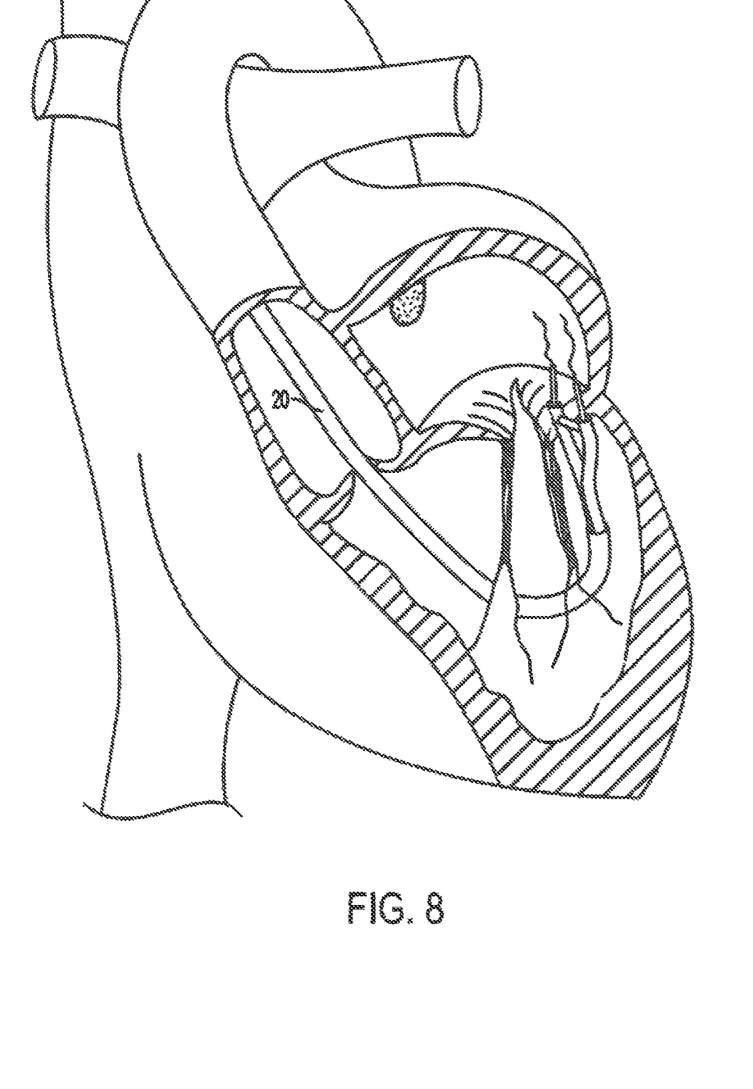
FIG. 8 is a view during implantation of the anchoring elements of the catheter for placing the anchoring elements.

The central branch 10, in the example shown, has a shorter length than the predetermined implantation distance of the two anchoring elements 2, so that the linking element 3, when placed, brings the two anchoring elements 2 to which it is connected closer together, as can be seen by comparing FIGS. 2 and 6, which respectively depict the beginning and completion of placement of the linking element of this example.

As shown in FIGS. 1 to 4, the wire of which linking element 3 of these Figures is made has at each end of the central branch 10, two successive bends at right angles to each other. This wire may then be rounded at the intermediate portion 13 to form a receptacle 15 that can receive a turn 5 with a tight fit.

One of the side branches 11 extends from the corresponding intermediate portion 13 on one side of the central branch 10, while the other side branch 11 extends from the other intermediate portion 13, on the opposite side of the central branch 10.

Figure 3:
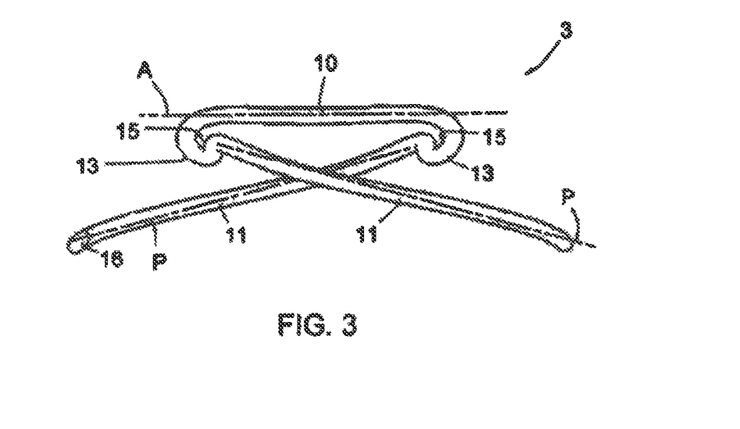
FIG. 3 is a side view of the linking element on an enlarged scale.

FIG. 3 shows that the side branches 11 may extend substantially in planes P oriented obliquely with respect to the lengthwise axis A of the central branch 10 so that each free end of a side branch 11 is located at a distance from the lengthwise axis A in a direction perpendicular to the lengthwise axis A. FIG. 1 shows that each branch 11 can thus be engaged on the corresponding turn 5 of an anchoring element 2 while the central branch 10 is at a distance from the plane in which the turn 5 extends.

Figure 4:
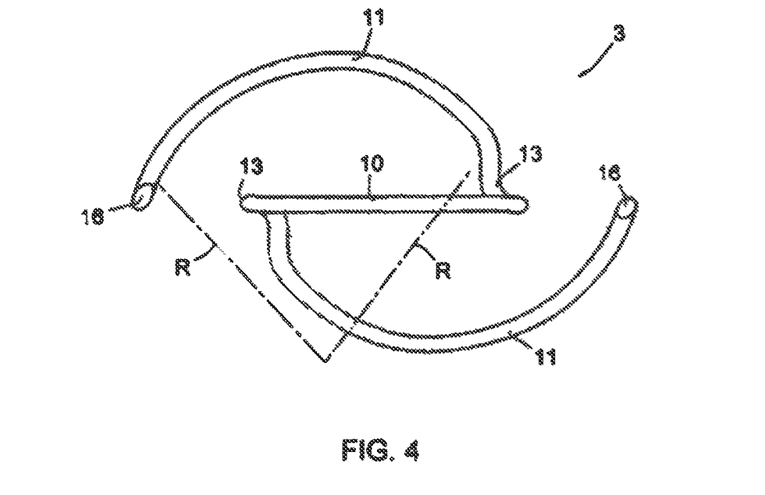
FIG. 4 is a top view of the linking element.

FIG. 4 shows that each side branch 11 may extend over an arc delimited by radii R which form between them an angle of preferably approximately sixty to ninety degrees, so that the length of the side branch 11 is such that the free end of the side branch 11 is in the extension of the lengthwise axis A of the central branch 10.

The free ends of the side branches 11 preferably have bevels 16 that make them sharp and, as shown in FIG. 6, the lengths of the side branches 11 may be such that the free end portions of the side branches 11 can become more or less inserted into the tissue 100 in the interconnection position of the anchoring elements 2 by the linking element 3.

The aforesaid implantation catheter 20 preferably places the two anchoring elements 2 in two holes that have previously been created in the tissue 100 and/or in the heart wall next to the annulus and that are provided at a distance from each other corresponding to the predetermined implantation distance of the two anchoring elements 2. A mandrel 22 may hold and screw a first anchoring element 2, in which the mandrel 22 is engaged, in one of the holes, and a mandrel 24 may hold and screw a second anchoring element 2, which is engaged in the other hole. The implantation catheter 20 may for example implant the two anchoring elements in the tissue and/or in the heart wall next to the annulus from a position that is superior to the annulus. The two holes may be created by a needle arrangement that pierces the tissue and/or heart wall next to the annulus from a position that is inferior to the annulus. For example, the two holes may be created using a third catheter and a needle arrangement, in which each hole is created by piercing the tissue 100 and/or heart wall next to the annulus with a needle from a position that is inferior to the annulus. The third catheter may for example be a wishbone catheter. The implantation catheter 20 may also for example be a wishbone catheter. The holes may also be created using the implantation catheter 20 and a needle arrangement, which may also be used to extend a guidewire through each hole to provide guidance from a position superior to the annulus for the anchor implantation catheter and the linking element placement catheter.

Figure 9A:
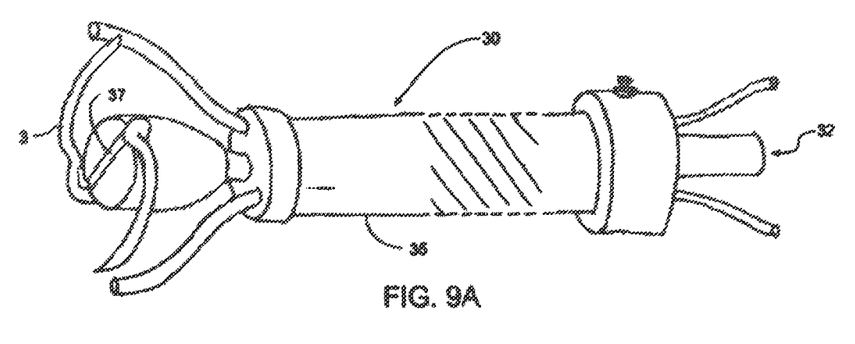
FIGS. 9A and 9B are views of the catheter for placing the linking element.
Figure 9B:
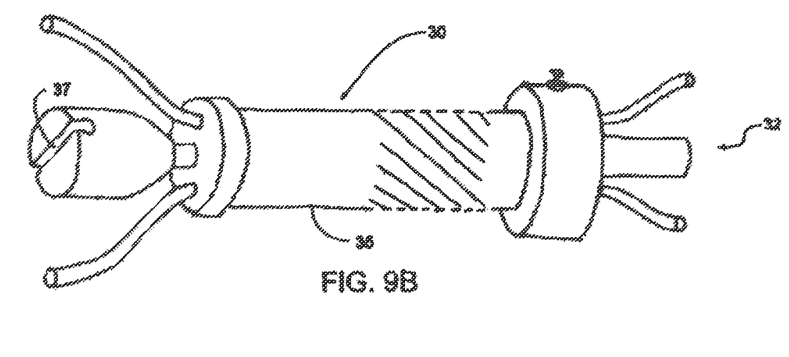
Figure 10:
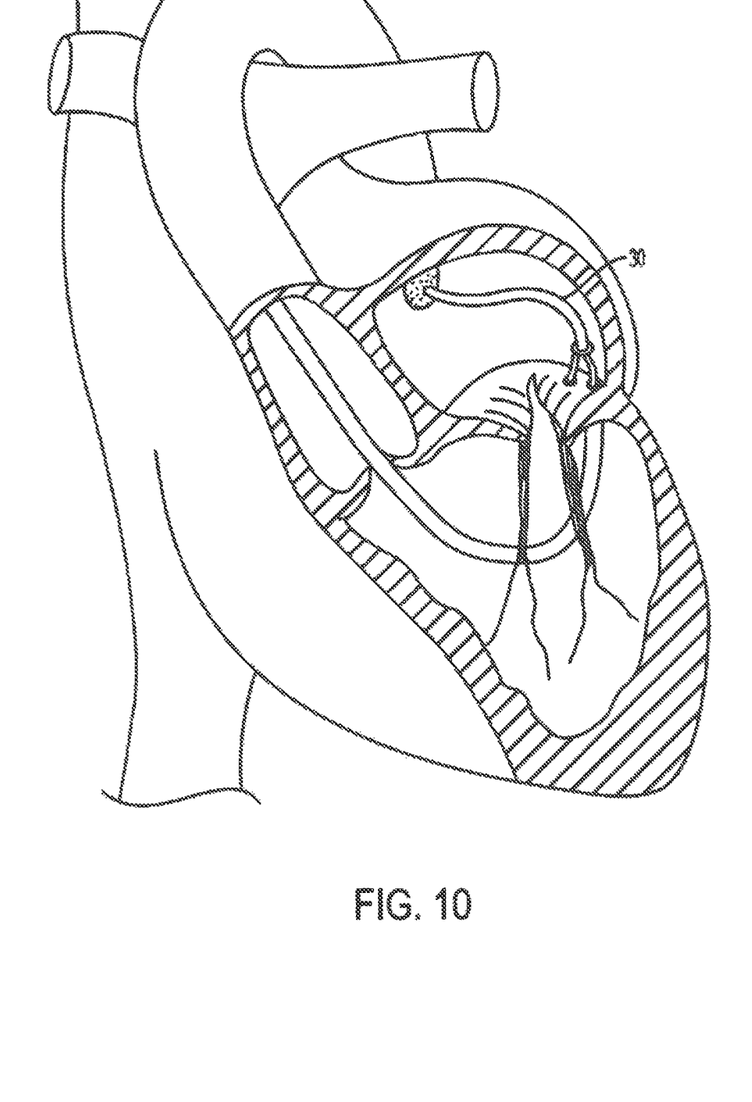
FIG. 10 is a view during implantation of the linking element of the catheter of the catheter for placing the linking element.

The catheter 30 for inserting and placing the linking element 3 preferably has a mandrel 32 engaged in a sheath 35, that can pivot with respect to the sheath 35, the mandrel 32 having, at its distal end, a diametrical groove 37 receiving, in a tightly fitting manner, the branch 10 of a linking element 3 such that there is a reversible link between the mandrel 32 and the linking element 3. The mandrel 32 can then be slid axially with respect to the sheath 35 in order to extract the side branches 11 from the sheath 35. Then, after engagement of these side branches 11 on the turns 5 of the anchoring elements 2, the mandrel 32 can be pivoted to effect the pivoting of the linking element 3 and hence the interconnection of the anchoring elements 2. The mandrel 32 can then be moved back with respect to the sheath 35 in order to be separated from the central branch 10. As shown in FIG. 10, the catheter 30 may insert and place the linking element 3 from a position that is superior to the annulus.

Figure 5:
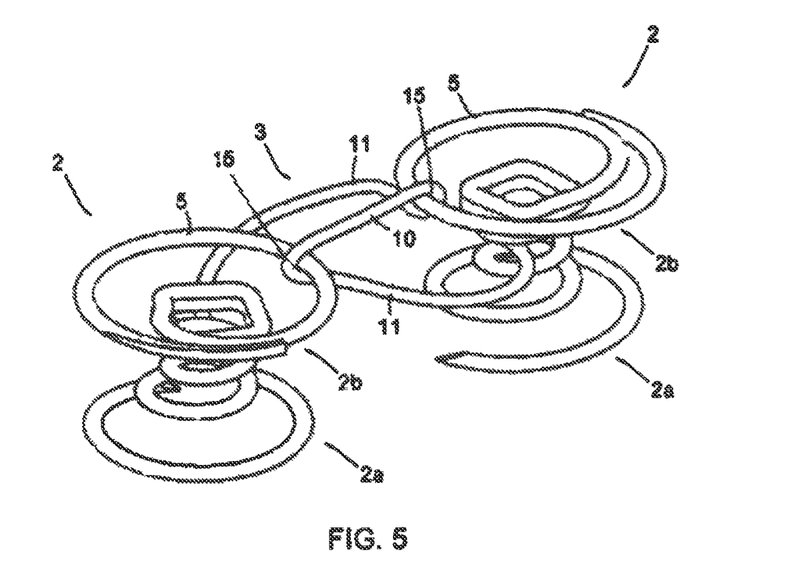
FIG. 5 is a view similar to that in FIG. 1 after the linking element has been placed on the anchoring elements, with the linking element thus creating an interconnection of the anchoring elements.

In practice, the anchoring elements 2 are set in place in the tissue 100 at a predetermined distance from each other, such as by use of said implantation catheter 20, then the linking element 3 is introduced such as by use of the aforesaid insertion and placement catheter 30. The linking element 3 is positioned as shown in FIGS. 1 and 2, namely with the free ends 16 of the side branches 11 engaged inside the turns 5. The linking element 3 is then pivoted perpendicular to the central branch 10 so as to slide the side branches 11 along the respective turns 5 until the anchoring elements 2 are in the interconnection position shown in FIGS. 5 and 6, in which the ends of the central branch 10 are located near the turns 5 and the turns 5 are engaged in the respective receptacles 15 in the linking element 3.

In the interconnection position, the anchoring elements 2 have been brought closer to each other, as shown in FIG. 6, so that the apparatus according to the invention effects a contraction 110 of the valve annulus and hence an annuloplasty.

Maintenance of the interconnection position may be ensured by reception of the turns 5 in the receptacles 15 as well as by the insertion of the free end portions of the side branches 11 in the tissue 100.

As apparent from the foregoing, embodiments of the apparatus and methods for treatment of a heart valve, in particular a heart mitral valve, can allow either annuloplasties, when the central branch 10 has a length less than the predetermined implantation distance of the anchoring elements 2, or reinforcement of the valve annulus when the central branch 10 has a length substantially equal to the predetermined distance, in a relatively simple and rapid manner, by a minimally invasive percutaneous procedure.

The apparatus and methods thus have decisive advantages over existing devices and techniques.

The apparatus, systems and methods described above with reference to preferred embodiments, are merely examples. It goes without saying that they are not confined to the depicted embodiment. For example, the wire from which an anchoring element 2 is formed can have a circular cross section as shown, or a square or rectangular cross section; the turn 5 can be circular in shape as shown or can have any other shape elliptical for example; the turn 5 of an anchoring element 2 can be in the shape of a ring, a loop, or any other structure able to form a support surface for the linking element 3, etc.

What is claimed is:

1. A method for treating a heart valve, the method comprising:
   introducing at least two anchoring elements percutaneously through a delivery catheter, the at least two anchoring elements each including a support surface;
   positioning the at least two anchoring elements adjacent to a heart valve to be treated;
   advancing the at least two anchoring elements such that the at least two anchoring elements penetrate an annulus of the heart valve and/or a heart wall next to the annulus at target locations that are different from each other; and
   interconnecting the at least two anchoring elements with a linking element,
   wherein the linking element comprises a central branch having two ends and two side branches, wherein the side branches are longer than the central branch, and wherein a receptacle is formed between the central branch and each of the two side branches, the receptacle being configured to receive and retain the respective support surface of the anchoring elements.

2. The method according to claim 1, wherein the step of interconnecting comprises engaging each of the two side branches of the linking element with a said support surface of a different one of the at least two anchoring elements.

3. The method according to claim 2, wherein the engaging of the two side branches of the linking element with the support surfaces of the at least two anchoring elements causes the linking element to be pivotably entrained such that ends of the central branch are brought near the support surfaces of the at least two anchoring elements that the two side branches respectively engage.

4. The method according to claim 3, wherein positioning and the pivoting entrainment of the linking element are caused by a mandrel that is engaged in a sheath, wherein the mandrel can pivot with respect to the sheath.

5. The method according to claim 4, wherein the mandrel includes a diametrical groove and a distal end, and the diametrical groove receives the central branch of the linking element such that there is a reversible link between the mandrel and the linking element.

6. The method according to claim 5, wherein the interconnecting step further comprises:
   sliding the mandrel axially with respect to the sheath, such that the side branches are extracted from the sheath;
   engaging the side branches with a turn of the at least two anchoring elements; and
   pivoting the mandrel to effect the pivoting of the linking element.

7. The method according to claim 1, wherein the two side branches are two curved side branches.

8. The method according to claim 1, wherein the linking element is shorter than a distance between the anchoring elements at the target locations, and the interconnecting step causes the annulus to be constricted.

9. The method according to claim 1, wherein the linking element is of the same length as a distance between the anchoring elements at the target locations, and the interconnecting step causes the annulus to be reinforced without being constricted.

10. A method for treating a heart valve, the method comprising:
    percutaneously advancing a catheter to a treatment site near a heart valve to be treated;
    introducing at least two anchoring elements percutaneously through a delivery catheter at different locations into an annulus of the heart valve and/or a heart wall; and
    connecting the at least two anchoring elements with a linking element,
    wherein the linking element comprises a central branch having two ends and two side branches, wherein the side branches are longer than the central branch, and wherein a receptacle is formed between the central branch and each of the two side branches, the receptacle being configured to receive and retain a respective support surface of the anchoring elements.

11. The method according to claim 10, wherein connecting the at least two anchoring elements with the linking element comprises:
    engaging a first side branch of the linking element with a support surface of a first anchoring element, and engaging a second side branch of the linking element with a support surface of a second anchoring element; and
    rotating the linking element until a first receptacle engages the support surface of the first anchoring element, and a second receptacle engages the support surface of the second anchoring element.

12. The method according to claim 10, comprising introducing at least three anchoring elements, and connecting the at least three anchoring elements such that the at least three anchoring elements are connected in a series with two ends.

13. The method according to claim 10, comprising introducing at least three anchoring elements, and connecting the at least three anchoring elements such that a closed loop is formed.

* * * * *